(12) United States Patent
Su et al.

(10) Patent No.: US 7,974,157 B2
(45) Date of Patent: Jul. 5, 2011

(54) METHOD FOR FORMING AN APPARATUS FOR INDICATING THE PASSAGE OF TIME AND THE FORMED APPARATUS

(75) Inventors: Wei-Fang Su, Taipei (TW); Yulia Galagan, Taipei (TW)

(73) Assignee: Wei-Fang Su, Taipei (TW)

( * ) Notice: Subject to any disclaimer, the term of this patent is extended or adjusted under 35 U.S.C. 154(b) by 0 days.

(21) Appl. No.: 12/835,806

(22) Filed: Jul. 14, 2010

(65) Prior Publication Data

US 2010/0275835 A1  Nov. 4, 2010

Related U.S. Application Data

(62) Division of application No. 11/949,613, filed on Dec. 3, 2007, now Pat. No. 7,791,984.

(30) Foreign Application Priority Data

Dec. 8, 2006 (TW) .............................. 95145956 A

(51) Int. Cl.
*G04F 1/00* (2006.01)
*G01N 21/00* (2006.01)
(52) U.S. Cl. ........................................ 368/327; 116/206
(58) Field of Classification Search .................... 368/89, 368/113, 327; 116/200, 206; 374/102–103; 422/50, 400–402; 426/87–88
See application file for complete search history.

(56) References Cited

U.S. PATENT DOCUMENTS

| 3,999,946 | A | * | 12/1976 | Patel et al. | 422/400 |
| 4,195,056 | A | * | 3/1980 | Patel | 422/416 |
| 4,812,053 | A | * | 3/1989 | Bhattacharjee | 374/102 |
| 5,045,283 | A | * | 9/1991 | Patel | 422/424 |
| 5,719,034 | A | | 2/1998 | Kiser et al. | |
| 5,756,356 | A | * | 5/1998 | Yanagi et al. | 436/7 |
| 6,103,351 | A | | 8/2000 | Ram et al. | |
| 6,113,857 | A | | 9/2000 | Manico et al. | |
| 6,452,873 | B1 | | 9/2002 | Holt et al. | |
| 7,280,441 | B2 | | 10/2007 | MacDonald et al. | |
| 7,294,379 | B2 | * | 11/2007 | Ko et al. | 428/40.1 |
| 7,372,780 | B1 | | 5/2008 | Braunberger | |
| 7,434,535 | B2 | * | 10/2008 | Adamy | 116/206 |
| 7,776,371 | B2 | * | 8/2010 | Ribi | 426/87 |
| 2005/0141348 | A1 | | 6/2005 | Adamy | |
| 2005/0185520 | A1 | | 8/2005 | Haas et al. | |
| 2009/0266291 | A1 | | 10/2009 | Braunberger | |

* cited by examiner

*Primary Examiner* — Vit W Miska
(74) *Attorney, Agent, or Firm* — WPAT, PC; Justin King

(57) ABSTRACT

The present invention discloses a time passage indicating apparatus which comprises a substrate, a background layer on the substrate, and a time passage indicating layer on the background layer. The background layer and the time passage indicating layer bond to each other through a first and second polymer binder. The background layer displays a background color. The time passage indicating layer displays an initial color in an initial state that is different from the background color, and a final color in a final state that is substantially the same as the background color, so as to indicate the end of a time period where the time passage indicating layer transforms from the initial state to the final state.

10 Claims, 12 Drawing Sheets

US 7,974,157 B2

METHOD FOR FORMING AN APPARATUS FOR INDICATING THE PASSAGE OF TIME AND THE FORMED APPARATUS

CROSS REFERENCE TO RELATED APPLICATIONS

This is a divisional of U.S. Ser. No. 11/949,613, filed Dec. 3, 2007 by the same inventors, and claims priority there from. This divisional application contains rewritten claims to the restricted-out subject matter of original claims.

BACKGROUND OF THE INVENTION

1. Field of the Invention

The present invention is generally related to a time-indicating apparatus, and more particularly to a method of forming an apparatus for indicating the passage of time and the formed apparatus.

2. Description of the Prior Art

Generally, food is considered to be safe within the shelf life. However, it is generally not true. For instance, the temperature of the environment for storing food is so high or the time of the food exposing to air is so long to result in bacterial overgrowth or food spoilage and thereby to affect human health. In order to avoid consumers from eating spoiled food, new packaging technology to indicate the state of food has been researched by various companies and academic organizations. For example, a time-temperature indicator (TTI) has a function of indicating the temperature and time variations of a product (such as food) undergoing the processes of storage, transportation, and sale by color change. It can indicate the degree of quality decrease due to the temperature and time variations of a product from the time of completing fabrication until the time of utilization so as to ensure the safety of the product.

At present, such commercialized products comprise VIT-SAB®, Life Lines®, 3M™, DeltaTrak®, OnVu™ and so forth. Their operation principles comprise enzyme catalysis, diffusion mechanism, solid-state polymerization, etc. These products have disadvantages of inconvenience in usage and high cost. Therefore, developing a novel apparatus for indicating the passage of time is required to fulfill usage convenience, precise indication, and low cost.

SUMMARY OF THE INVENTION

Therefore, in accordance with the previous summary, objects, features and advantages of the present disclosure will become apparent to one skilled in the art from the subsequent description and the appended claims taken in conjunction with the accompanying drawings.

In light of the above mentioned background, the present invention provides a method of forming an apparatus for indicating the passage of time and the formed apparatus to overcome the above disadvantages in the prior art.

One feature of the present invention is to disclose an apparatus for indicating the passage of time. The provided apparatus functions through the change in color of a time passage indicating material which displays a different color in its oxidized and reduced states, respectively. The color of the time passage indicating material continuously fades throughout the oxidation process; after a time period of a predetermined length, the color of the time passage indicating material becomes substantially the same a background color, rendering an effect that the time passage indicating material disappears from the background layer, thereby indicating the end of the time period.

One embodiment of the present invention discloses a method for forming the time passage indicating apparatus. Appropriate polymer binders are selected for the time passage indicating material and the background layer material to bond to each other, so the time passage indicating layer can be easily formed on the background layer by simple coating and curing procedures. Therefore, the present invention is suitable for economic industrial usage.

Accordingly, the present invention discloses an apparatus for indicating the passage of time. The provided apparatus comprises a substrate, a background layer formed on the substrate, and a time passage indicating layer formed on the background layer, wherein the time passage indicating layer and the background layer bonds to each other through physical or chemical bonds. The color of the time passage indicating layer is different from the background in an initial state and substantially the same as the background in a final state; when the final state is reached, the time passage indicating layer becomes visually unidentifiable on the background layer, rendering an effect that the time passage indicating layer disappears from the background layer, thereby indicating the end of the time period.

BRIEF DESCRIPTION OF THE DRAWINGS

The accompanying drawings incorporated in and forming a part of the specification illustrate several aspects of the present invention, and together with the description serve to explain the principles of the disclosure. In the drawings.

DETAILED DESCRIPTION OF THE PREFERRED EMBODIMENTS

Figure 1:
FIG. 1 is an illustration of the provided time passage indicating apparatus functioning.

The present disclosure can be described by the embodiments given below. It is understood, however, that the embodiments below are not necessarily limitations to the present disclosure, but are used to a typical implementation of the invention.

Having summarized various aspects of the present invention, reference will now be made in detail to the description of the invention as illustrated in the drawings. While the invention will be described in connection with these drawings, there is no intent to limit it to the embodiment or embodiments disclosed therein. On the contrary the intent is to cover all alternatives, modifications and equivalents included within the spirit and scope of the invention as defined by the appended claims.

It is noted that the drawings presents herein have been provided to illustrate certain features and aspects of embodiments of the invention. It will be appreciated from the description provided herein that a variety of alternative embodiments and implementations may be realized, consistent with the scope and spirit of the present invention.

It is also noted that the drawings presents herein are not consistent with the same scale. Some scales of some components are not proportional to the scales of other components in order to provide comprehensive descriptions and emphasizes to this present invention.

The technical terminology that will be used herein are defined as follows: oxygen-permeable: with an oxygen-permeability greater than 1 ppm; oxygen-impermeable: with an oxygen-permeability equal to or lower than 1 ppm; and oxygen-free environment: with environment oxygen concentration lower than 1 ppm.

The first embodiment of the present invention discloses a method for forming an apparatus for indicating the passage of time. First, a background layer material is provided, which comprises a first polymer binder, a base material and a background layer color rendering material, wherein the base material is colorless and the background layer color rendering material displays a background color. Detail of the first polymer binder and the background layer color rendering material will be described later.

Next, have the background layer coated and dried on a substrate to form a background layer on the substrate, wherein the background layer displays the background color. The material of the substrate comprises one selected from the group consisting of the following, or any combination thereof: aluminum metallized plastic, aluminum metallized paper, metal oxide coated plastic, metal oxide coated paper, glass, metal, plastic, and paper.

Then, a time passage indicating material is provided, which comprises a solvent, a redox compound, a reducing agent, and a second polymer binder. The solvent can be a hydrophilic substance, such as water, alcohol, or any combination thereof. The redox compound displays an initial color in an initial reduced state and a final color in a final oxidized state, wherein the initial color is different from the background color and the final color is substantially the same as the background color. The reducing agent exists in the time passage indicating material with a predetermined composition so as to reduce the redox compound to the initial reduced state. The reducing agent can be sodium hydrosulfite or a mixture of sodium hydrosulfite and alkaline medium.

It is noticed that in this embodiment, the background layer color rendering material is selected based on the redox compound. In one example, the redox compound comprises anthraquinone and derivatives thereof; therefore, the background layer color rendering material should be selected to also comprise anthraquinone and derivatives thereof. In another example, the redox compound comprises anthraquinone with at least one substituent wherein the substituent comprises one selected from the group consisting of the following, or any combination thereof: ulfonic acid, hydrogen, alkyl, aryl, carboxyl, acyl, alkoxy, and halide; therefore, the background layer color rendering material should be selected to also comprise one selected from the group consisting of the following, or any combination thereof: ulfonic acid, hydrogen, alkyl, aryl, carboxyl, acyl, alkoxy, and halide. The better selection for the redox compound and the background layer color rendering material comprises one selected from the following, or any combination thereof: anthraquinone, anthraquinone-2-sulfonic acid, anthraquinone-2-sulfonic sodium salt, anthraquinone-2-sulfonic monohydrate, 1-anthraquinonesulfonic acid, 1-anthraquinonesulfonic sodium salt, anthraquinone-2,6-disulfonicacid, anthraquinone-2,6-disulfonic disodium salt, anthraquinone-1,5-disulfonic acid, anthraquinone-1,5-disulfonic disodium salt, and anthraquinone-1,5-disulfonic hydrate.

Next, have the time passage indicating material coated and dried on the substrate to form a time passage indicating layer on the substrate. The time passage indicating layer occupies a smaller portion of the background layer, and the time passage indicating layer binds to the background layer through physical or chemical bonding formed between the first and second polymer binder.

The coating procedure can be spin coating, spray coating, printing, knife coating, or dip coating. Moreover the coating and drying procedures are carried out in an oxygen-free environment.

The first and second polymer binder can be water-soluble or dispersible in water; the better selection for the first and second polymer binder comprises one selected from the group consisting of the following, or any combination thereof: polyvinyl alcohol, methylcellulose, hydroxyethylcellulose, hydroxypropylcellulose, carboxymethyl cellulose, and polyethylene glycol.

Referring to FIG. 1, which is an illustration of how the provided apparatus for indicating time passage works. After the apparatus is formed, all the redox compound in the time passage indicating layer is reduced to the initial reduced state, and later when the time passage indicating material is oxidized through contact with oxygen molecules, the time passage indicating layer gradually transforms from the initial reduced state to final oxidized state, and the color of the time passage indicating layer changes from the initial color to the final color. When the final oxidized state is reached, the time passage indicating layer becomes visually unidentifiable on the background layer, indicating the end of the time passage to be indicated.

In a preferred example of this embodiment, an oxygen-permeable protection layer is formed on the background layer after the time passage indicating layer has been formed. The protection layer covers the time passage indicating layer and has at least one transparent portion so that the change in color of the time passage indicating layer is observable from the exterior of the protection layer. The forming process of the protection layer comprises: providing a protection layer material which comprises at least one acrylate and an initiator. Then, coat and cure the protection layer material on the background layer to form the protection layer on the background layer, wherein the curing procedure can be carried out by thermal curing or light curing method. The above coating and curing procedure is carried out in an oxygen-free environment.

The protection is further preferred to comprise an oxygen-scavenging material, which exists in the protection layer material with a predetermined composition. The oxygen-scavenging material comprises one selected from the group consisting of the following, or any combination thereof: reduced metal, tannins, sulfite, ascorbate, reduced form of quinine and anthraquinone derivative, photoreducible carbonyl compound, and oxidizable organic compound.

In another preferred example of this embodiment, an oxygen-impermeable wrapper is utilized to wrap the formed time indicating apparatus in an oxygen-free environment. The wrapper is to prevent the provided apparatus from contact with the ambient oxygen molecule. Once the unwrapped, the provided apparatus is activated. The wrapper is preferred to have a gas barrier film filled with a sealing layer, wherein the material of the gas barrier film comprises one selected from the group consisting of the following, or any combination thereof: metal foil, metal oxide, carbon, $SiO_x$, polyester, polyamide, polyvinyl chloride, polyvinylidene chloride, polyethylene naphthalate, polyacrylonitrile, polycarbonate, polyether, polyimide, polysulfone, rubber, and epoxy resin. The material of the sealing layer comprises one selected from the group consisting of the following, or any combination thereof: polyester, polypropylene, polyvinyl alcohol, polyvinyl acetate, rubber, epoxy resin, and polyethylene.

The objective of the disclosed method is to form an apparatus for indication of the time passage through color change of a time passage indicating material when oxidized with ambient oxygen molecules penetrating through the protection layer. The penetration rate is contingent upon the composition of the protection layer material, and the total amount of oxygen coming through the protection layer per unit time can be estimated through the above penetration rate along with the surface area of the protection layer. In other words, the total amount of oxygen that shall come through the protection layer in a predetermined period of time can be controlled by selecting the material and surface area of the protection layer to be made. In addition, the substrate can be selected to be oxygen permeable or impermeable; when the substrate is oxygen-permeable, there are two channels for oxygen to penetrate into the time indicating apparatus, which is to through the protection layer and the substrate, respectively. In such case, as discussed above, the material and surface area of the substrate must be taken into consideration as well to precisely estimate the total amount of oxygen reaching the time passage indicating layer, so as to control the length of time the provided apparatus can indicate.

On the other hand, the degree of reduction of the redox compound in the initial reduced state, thus the overall time needed for the redox compound to be oxidized to the final oxidized state (the time point where the time passage indicating layer shall disappear on the background layer), can be controlled by selecting the chemical composition of the reducing agent and amount thereof in the time passage indicating material. In addition, the power and amount of the oxygen-scavenging material in the protection layer can also be utilized to control the amount of oxygen that is reaching the time passage indicating layer.

To sum up, this embodiment discloses a method for forming an apparatus for indicating time passage, wherein the length of time that can be indicated by the provided apparatus is controlled by the following factors: (1) the penetration rate of oxygen through the protection layer which is dependent on the chemical composition of the protection layer; (2) the total amount of oxygen coming through the protection layer per unit time which is dependent on the surface area of the protection layer; (3) the penetration rate of oxygen through the substrate which is dependent on the chemical composition of the substrate; (4) the total amount of oxygen coming through the substrate per unit time which is dependent on the surface area of the substrate; (5) the degree of reduction of the redox compound at the beginning of the time period to be indicated, which is dependent on the chemical composition and the amount of the reducing agent in the time passage indicating material; and (6) the real amount of oxygen that is reaching the time passage indicating layer per unit time, which is dependent on the composition and amount of the oxygen-scavenging material in the protection layer.

Figure 2A:
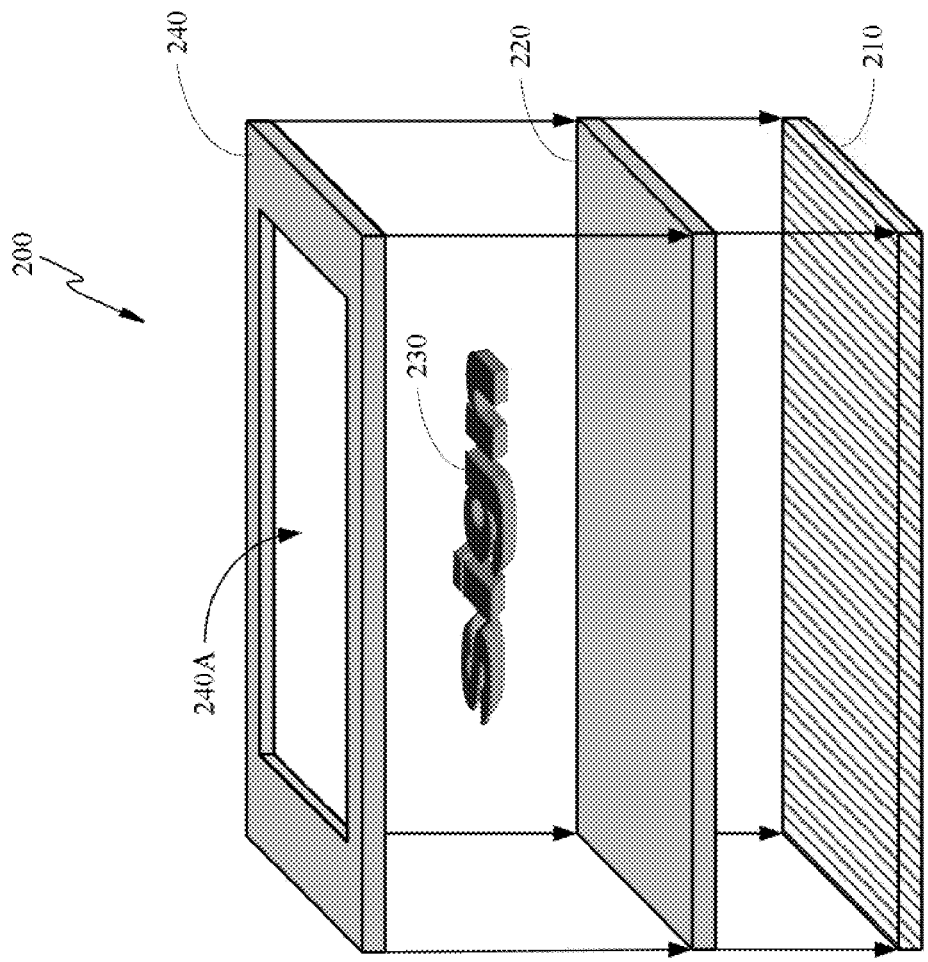
FIGS. 2A and 2B are schematic of the provided time passage indicating apparatus according to the second embodiment of the present invention.
Figure 2B:
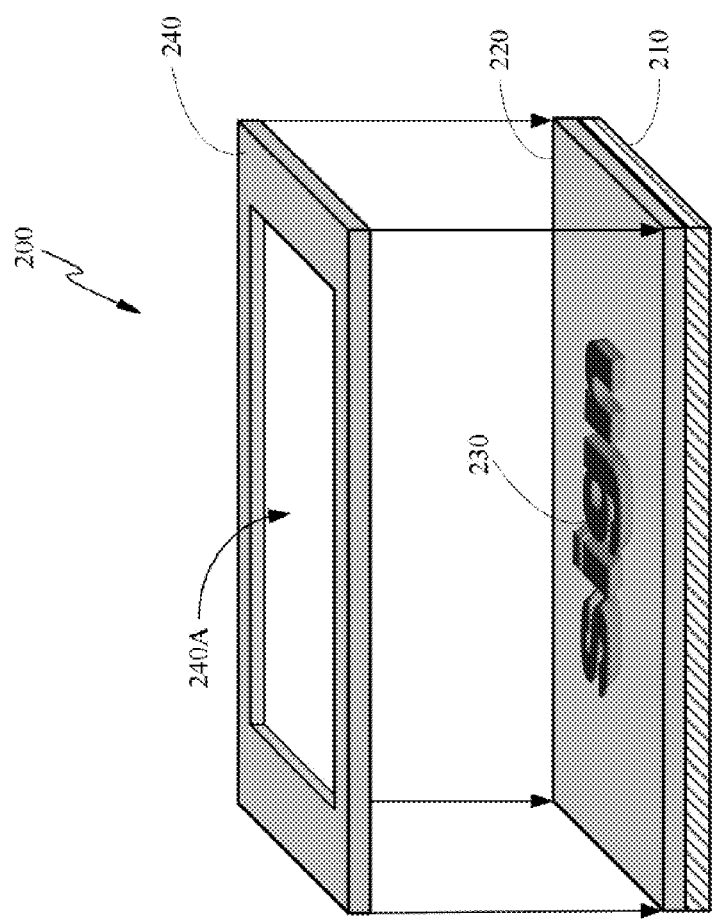

The second embodiment of the present invention discloses an apparatus for indicating the time passage. Referring to FIG. 2A, time passage indicating apparatus 200 comprises a substrate 210, a background layer 220 formed on the substrate 210, and a time passage indicating layer 230 formed on the background layer 220. The time passage indicating apparatus 200 optionally comprises a protection layer 240 which has at least one transparent portion 240A. It is noted that in the FIG. 2A, the time indicating layer 230 is an character "sign", but as understood by those skilled in the art, the time passage indicating layer 230 can be other shape, not limited to that in the figure. Referring to FIG. 2B, which shows the formed time passage indicating apparatus. The selection of the substrate 210 is the same as that in the first embodiment. The background layer 220 is made of a first polymer binder, a base material and a background layer color rendering material, wherein the base material is colorless and the background layer color rendering material displays a background color such that the background layer 220 displays the background color. The selection of the base material is the same as that in the first embodiment. The time passage indicating layer 230 only covers a portion of the background layer 220. The time passage indicating layer 230 is made of a solvent, a redox compound, a reducing agent and a second polymer binder, wherein the second polymer binder bonds with the first polymer binder through physical or chemical bonding. The selection of the solvent, first polymer binder, and second polymer binder is the same as that in the first embodiment. Also, the forming procedure of the time passage indicating layer 230 is the same as that in the first embodiment. The time passage indicating layer 230 has a initial state and a final state, wherein the time passage indicating layer 230 displays a initial color in the initial state and a final color in the final state. The initial color is different from the background color and the final color is substantially the same as the background color, such that when the final state is reached, the time passage indicating layer 230 becomes visually unidentifiable on the background layer, rendering an effect of the time passage indicating layer 230 disappearing from the background layer 230. The reducing agent exists in the time passage indicating material with a predetermined composition and a predetermined amount so as to reduce the redox compound to the initial state. The choice of the reducing agent is the same as that in the first embodiment. In addition, as in the first embodiment, the background layer color rendering material is selected based on the redox compound; in a preferred example, the selection of the redox compound and background layer color rendering material is the same as that in the first embodiment.

At the beginning of the time period to be indicated, all redox compound in the time passage indicating layer 230 has been reduced to the initial state, and later when the time passage indicating material is oxidized through contact with oxygen molecules, the time passage indicating layer gradually transforms from the initial state to the final state, and the color of the time passage indicating layer changes from the initial color to the final color, when the final state is reached, the time passage indicating layer becomes visually unidentifiable on the background layer, indicating the end of the time passage to be indicated.

In one preferred example of this embodiment, the time passage indicating apparatus 200 further comprises a protection layer 240, the protection layer 240 covers the time passage indicating layer 230, and the protection layer has at least one transparent portion 240A such that the color change of the time passage indicating layer 230 is observable from the exterior of the protection layer. The protection layer 240 is preferred to comprise an oxygen-scavenging material which exists in the protection layer material; the selection of the oxygen-scavenging material is the same as that in the first embodiment.

Another preferred example of this embodiment further comprises a wrapper layer which wraps up the formed time passage indicating apparatus 200. The wrapper layer is preferred to comprise an oxygen-impermeable wrapper; the selection of the wrapper material is the same as that in the first embodiment.

To sum up, this embodiment discloses a time passage indicating apparatus 200 through the color change of a time passage indicating layer 230 during oxidation. The length of time that can be indicated by the provided apparatus 200 is controlled by the following factors: (1) the penetration rate of oxygen through the protection layer 240 which is dependent on the chemical composition of the protection layer 240; (2) the total amount of oxygen coming through the protection layer 240 per unit time which is dependent on the surface area of the protection layer 240; (3) when the substrate 210 is oxygen permeable, the penetration rate of oxygen through the substrate 210 which is dependent on the chemical composition of the substrate 210; (4) when the substrate 210 is oxygen permeable, the total amount of oxygen coming through the substrate 210 per unit time which is dependent on the surface area of the substrate 210; (5) the degree of reduction of the redox compound at the beginning of the time period to be indicated, which is dependent on the chemical composition and the amount of the reducing agent in the time passage indicating material; and (6) the real amount of oxygen that is reaching the time passage indicating layer 230 per unit time, which is dependent on the composition and amount of the oxygen-scavenging material in the protection layer 240.

Example 1

Forming the Time Passage Indicating Apparatus (a) Preparation of background

The suitable composition for background in present invention contains: 10 g polyvinyl alcohol solution (20 wt % in an equiweight water-ethanol mixture) and 0.8 g Anthraquinone-2-sulfonic acid, sodium salt, monohydrate (AQS). The mixture was stirred for about 10 minutes.

Then, a 200 μm thin film is obtained on the glass substrate using a draw down rod. The sample is dried in oven at 70° C. After removing the solvent, a background film is obtained with a thickness of about 30 μm.

(b) Printing of Time Passage Indicating Material

The suitable composition of the time passage indicating material contains (1) the red-ox compound: Anthraquinone-2-sulfonic acid, sodium salt, monohydrate (AQS); (2) the reducing agent: Sodium hydrosulfite ($Na_2S_2O_4$), alkali (NaOH); (3) the solvent: water-ethanol mixture (1:1); and (4) the polymer binder: polyvinyl alcohol (PVA). The composition of the time passage indicating material is summed in the following table:

TABLE 1

Composition of time passage indicating material

| Substance | Amount(g) |
| --- | --- |
| AQS | 0.025 |
| $Na_2S_2O_4$ | 0.2 |
| NaOH (5M water solution) | 0.8 |
| PVA (20% in a 1:1 water-ethanol mixture) | 3 |

The mixture is first stirred for about 10 minutes in inert atmosphere to obtain a dark-red highly viscous solution. Next, a "sign" with a thickness of 100 μm is formed on the above mentioned background layer using a draw down rod and a stencil. The wet "sign" is dried with a hot gun. After removing the solvent, the thickness of the "sign" is about 15 μm. The printing and drying procedure is carried out in a glove-box filled with nitrogen (or argon); the oxygen concentration in the glove box is lower than 1 ppm.

(c) Formation of the Protection Layer

The "sign" and background layer is covered by a protection layer mainly comprising acrylates and photoinitiator. The composition of the protection layer is shown in Table 2.

TABLE 2

Composition of the protection layer

| Substance | Amount(g) |
| --- | --- |
| Propoxylated(2)neopentyl glycol diacrylate | 3 |
| 2-Hydroxyethyl methacrylate | 3 |
| Irgacure 651 | 0.12 |

The mixture of acrylates and photoinitiator (Irgacure 651) is first stirred about 10 minutes to form a solution. Then, a thin acrylate film with a thickness about 170 μm is made on top of the background and the "sign" using a draw down rod followed by a UV curing procedure (4-watts UVGL-25 Mineralight® lamp, λ=365 nm) for about 2 minutes. The UV-curing procedure is carried out in a glove box filled with nitrogen or argon. The oxygen concentration in the glove box is lower than 1 ppm.

Figure 3:
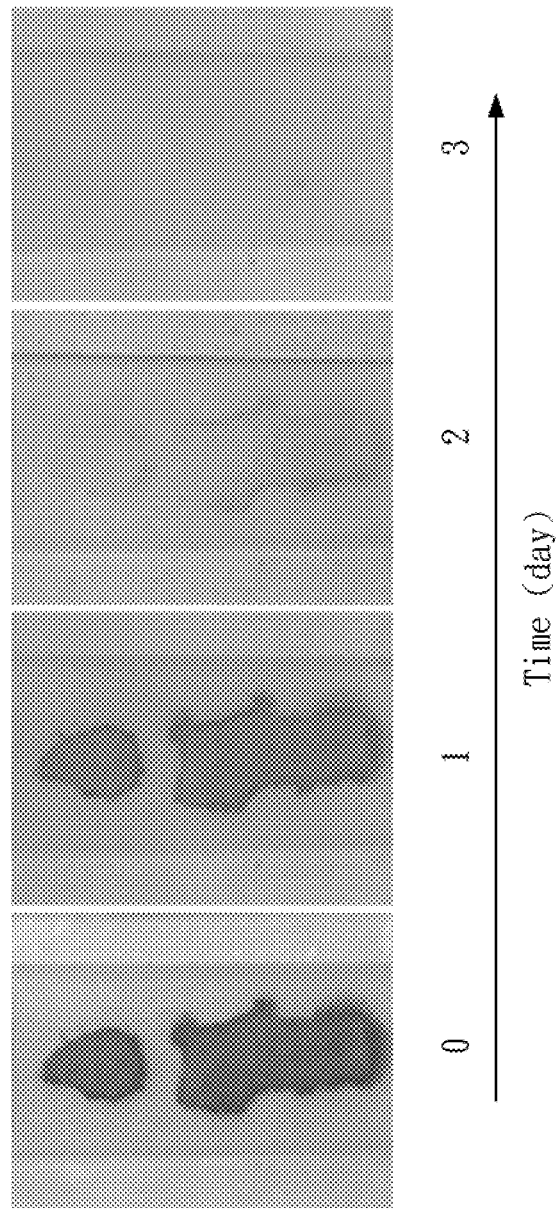
FIG. 3 is an illustration of the time passage indicating apparatus according to Example 1 functioning.

The obtained acrylate-coated "sign" is ready for time monitoring. Referring to FIG. 3, when it is put out in the air, the color of the "sign" will start to fade; such process gets complete in three days. At which time point, the color of the "sing" becomes beige-yellowish, which is the same color as the background layer, rendering an effect of the "sign" disappearing from the background layer.

Example 2

Effect of Composition of Time Passage Indicating Layer on the Color and Color Change Thereof This example will investigate the effect of the chemical composition of time passage indicating layer on the color and change in color of the time passage indicating layer.

(a) Alkali Concentration

The time passage indicating apparatus is prepared according to Example 1. Various composition of sodium hydroxide in the time passage indicating layer will be prepared and tested for its effect on the color and change in color of the time passage indicating layer. The base composition of the sample time passage indicating material is 3 g of Ethoxylated (15) trimethylolpropane Triacrylate, 3 g of 2-Hydroxyethyl methacrylate, and 0.12 g of photoinitiator (Irgacure651). The thickness of the sample film is 170 μm. The results are shown in Table 3.

TABLE 3

Effect of Alkali content on the color and change in color of the time passage indicating layer.

| Samples | Composition of time passage indicating layer | | | | Initial color of time passage indicating layer |
|---|---|---|---|---|---|
| | AQS (g) | $Na_2S_2O_4$ (g) | NaOH (5M) (g) | PVA (20%) (g) | |
| 2a.1 | 0.025 | 0.2 | 0.24 | 3 | yellow |
| 2a.2 | 0.025 | 0.2 | 0.4 | 3 | orange |
| 2a.3 | 0.025 | 0.2 | 0.8 | 3 | red |
| 2a.4 | 0.025 | 0.2 | 1.0 | 3 | red |

The color of the time passage indicating material depends on the amount of alkali. Without alkali or with small amount of alkali (sample 2a.1), the time passage indicating material has bright yellow color. Larger amount of alkali (sample 2a.2) gives orange color; further addition of alkali leads to dark-red color (examples 2a.3 and 2a.4).

Figure 4A:
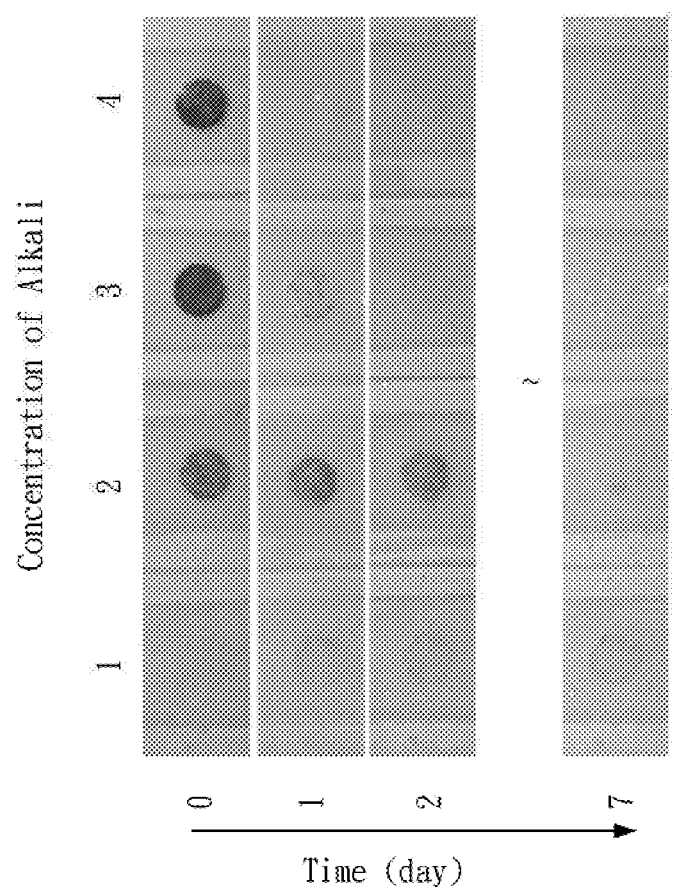
FIG. 4A shows the effect of Alkali concentration on color change of the time passage indicating layer tested in Example 2.

Referring to FIG. 4a, the time of color fading in the samples is different and it depends on the amount of alkali in the sample. Higher amount of alkali leads to faster color fading. Sample 2a.1 keeps its yellow color for up to 14 days; the color of sample 2a.2 becomes substantially the same as the background layer (which is the point defined as the end of the color fading period) in 7 days; the color fading time is 30 hours for sample 2a.3 and 20 hours for sample 2a.4. Take sample 2a.1 for instance, it has the slowest color fading rate among all samples, however, it provides poor time indication ability due to its indistinct color change from yellow to beige. Therefore, the preferred embodiment of the present utilizes high alkali content to increase the contrast between the color of the time passage indicating layer and the background layer, so as to achieve better time indication ability.

(b) Concentration of Reducing Agent

This test is similar to (a), only that the test target is changed to the amount of the reducing agent. The base composition of the sample time passage indicating material is 3 g of Ethoxylated (15)trimethylolpropane Triacrylate, 3 g of 2-Hydroxyethyl methacrylate, and 0.12 g of photoinitiator (Irgacure651). The thickness of the sample film is 170 μm. The results are shown in Table 4.

TABLE 4

Effect of the concentration of reducing agent on the color and color change of the time passage indicating layer

| Samples | Composition of time passage indicating layer | | | | Color fading time(day) |
|---|---|---|---|---|---|
| | AQS (g) | $Na_2S_2O_4$ (g) | NaOH (5M) (g) | PVA (20%) (g) | |
| 2b.1 | 0.025 | 0.2 | 0.24 | 3 | 2 |
| 2b.2 | 0.025 | 0.2 | 0.4 | 3 | 4 |
| 2b.3 | 0.025 | 0.2 | 0.8 | 3 | 6 |

Figure 4B:
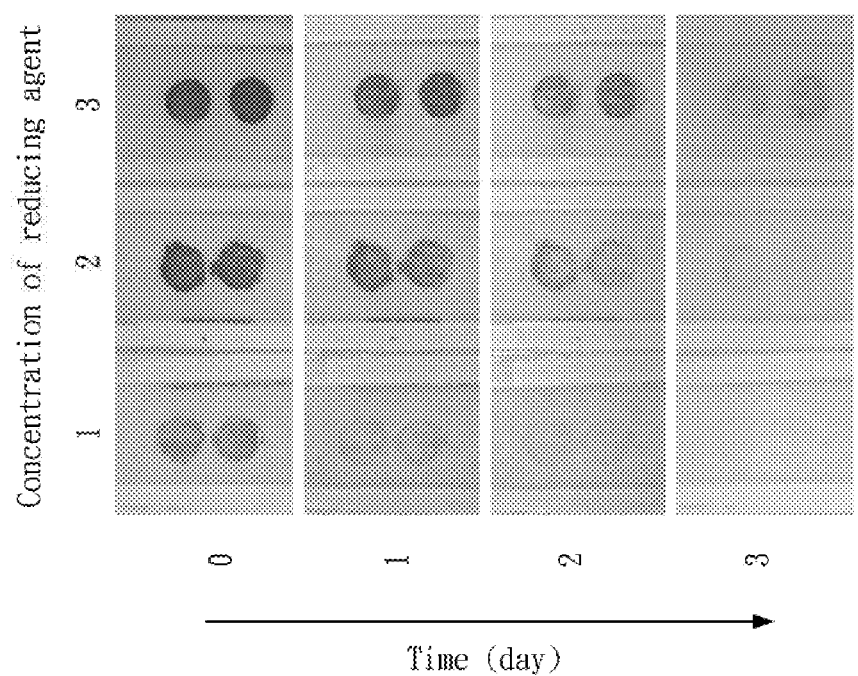
FIG. 4B shows the effect of the concentration of reducing agent on color change of the time passage indicating layer tested in Example 2.

Referring to FIG. 4b, the results shows higher reducing agent content leads to longer color fading time (with the end of color fading defined as when the color of the time indicating layer is substantially the same as the background layer).

Example 3

Figure 5:
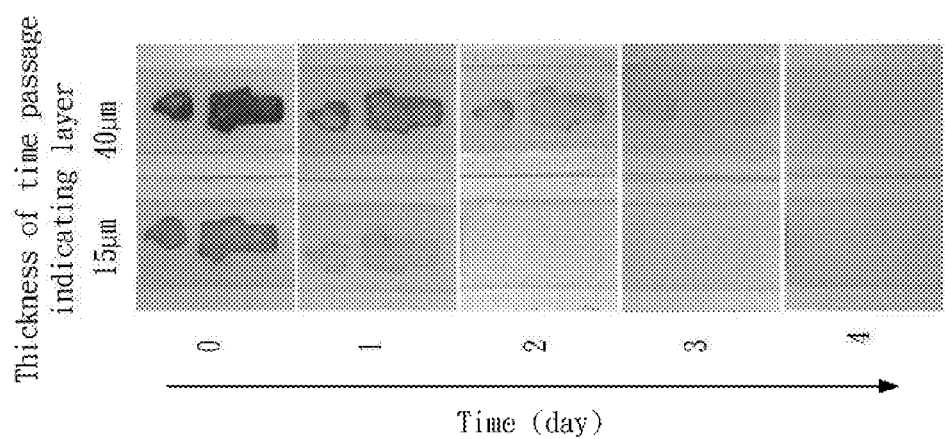
FIG. 5 shows the effect of the thickness of time passage indicating layer on color change thereof tested in Example 3.

Effect of Thickness of Time Passage Indicating Layer on the Color and Color Change Thereof This example measures the color fading time of two samples with time passage indicating layer thickness of 15 μm and 40 μm, respectively, so as to investigate the effect of thickness of time passage indicating layer on the color change of the time passage indicating layer. The base composition of the sample time passage indicating material is an equiweight mixture of Ethoxylated (15)trimethylolpropane Triacrylate and 2-Hydroxyethyl methacrylate, and 0.12 g of photoinitiator (Irgacure651). The thickness of the sample film is 170 μm. Referring to FIG. 5, the color fading time is 2 days for the 15 μm sample, and 5 days for the 40 μm sample.

Example 4

Figure 6:
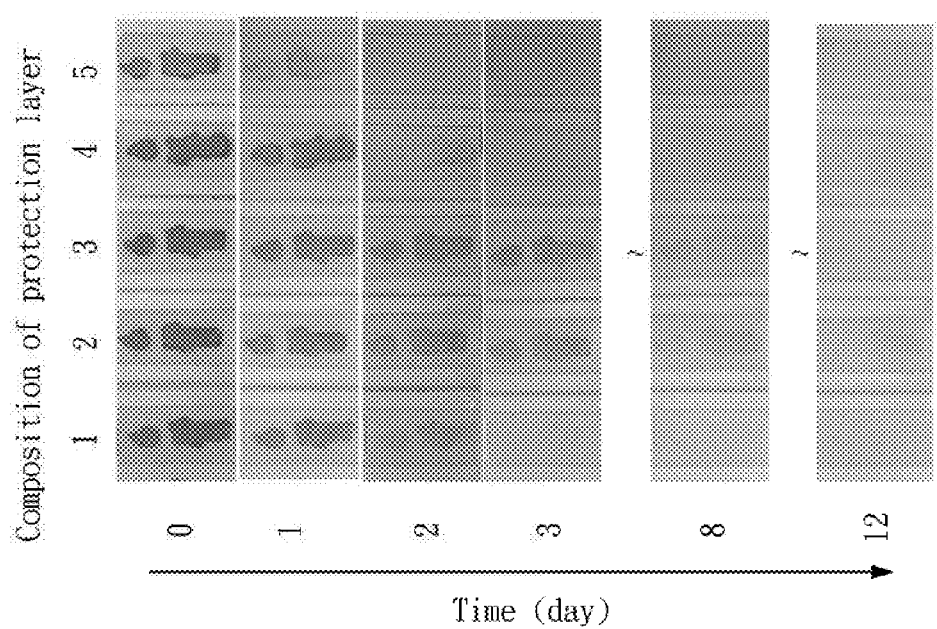
FIG. 6 shows the effect of the chemical composition of protection layer on color change of the time passage indicating layer tested in Example 4.

Effect of Composition of Protection Layer on the Color and Color Change of Time Passage Indicating Layer In this example, various composition of protection layer will be prepared and tested for its effect on the color and change in color of the time passage indicating layer. The base composition of the sample protection layer material is an equiweight mixture of two different acrylates, and 2 wt % of photoinitiator (Irgacure651). The thickness of the sample film is 170 μm. The time passage indicating apparatus is prepared according to Example 1. The results are shown in Table 5 and FIG. 6.

TABLE 5

Effect of protection layer composition on the color and color change of time passage indicating layer

| Samples | Composition of protection layer | Color fading time(day) |
|---|---|---|
| 4.1 | Tetraethylene Glycol Diacrylate/ 2-Hydroxyethyl methacrylate | 3 |
| 4.2 | Ethoxylated (2) Bisphenol A Dimethacrylate/ 2-Hydroxyethyl methacrylate | 14 |
| 4.3 | Tricyclodecane dimethanol diacrylate/ 2-Hydroxyethyl methacrylate | 12 |
| 4.4 | Propoxylated(2)neopentyl glycol diacrylate/ 2-Hydroxyethyl methacrylate | 3 |
| 4.5 | Ethoxylated(15)trimethylolpropane Triacrylate/ 2-Hydroxyethyl methacrylate | 2 |

Example 5

Effect of Thickness of Protection Layer on the Color and Color Change of Time Passage Indicating Layer This example measures the color fading time of two samples with protection layer thickness of 170 μm and 370 μm, respectively, so as to investigate the effect of thickness of protection layer on the color change of the time passage indicating layer. The base composition of the sample time passage indicating material is an equiweight mixture of Ethoxylated (15)trimethylolpropane Triacrylate and 2-Hydroxyethyl methacrylate, and photoinitiator (Irgacure 651). The forming process of the time passage indicating apparatus is the same as that in Example 1.

Figure 7:
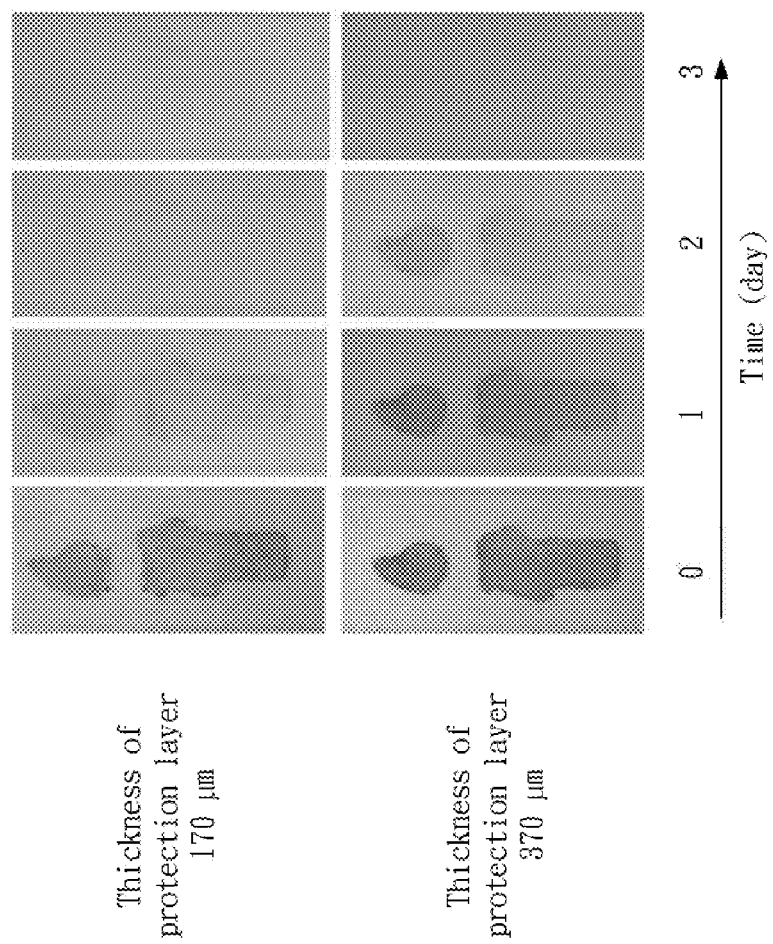
FIG. 7 shows the effect of the thickness of protection layer on color change of the time passage indicating layer tested in Example 5.

Referring to FIG. 7, it is shown that the color fading time (of which the end point is defined as when the color of the time passage indicating layer becomes substantially the same as that of the background layer) of the sample with protection layer thickness of 170 um is 2 days; the color of the sample with protection layer thickness of 370 um fades completely into the background after 3 days.

Example 6

Figure 8:
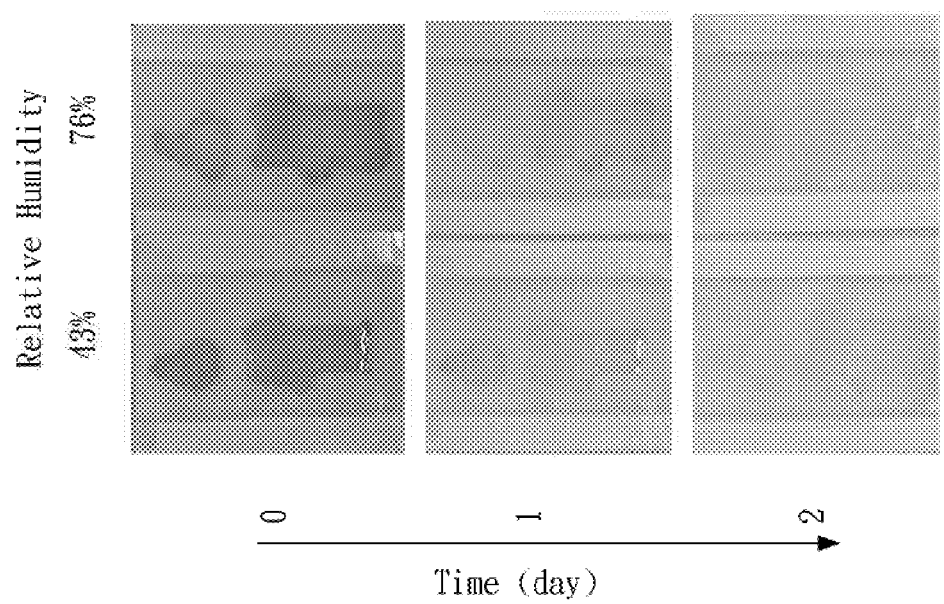
FIG. 8 shows the effect of ambient moisture on color change of the time passage indicating layer tested in Example 6.

Effect of Environment Moisture on Color Change of the Time Passage Indicating Layer This example investigates the effect of ambient moisture on the color change of the time passage indicating layer. The base composition of the sample time passage indicating material is an equiweight mixture of Ethoxylated (15)trimethylolpropane Triacrylate and 2-Hydroxyethyl methacrylate, and photoinitiator (Irgacure651) The forming process of the time passage indicating apparatus is the same as that in Example 1. The formed time passage indicating apparatus is placed in environment of 44% and 76% RH, respectively, for comparison. Referring to FIG. 8, the comparison results show that the color change of the time passage indicating layer is not affected by the ambient moisture.

Example 7

Figure 9:
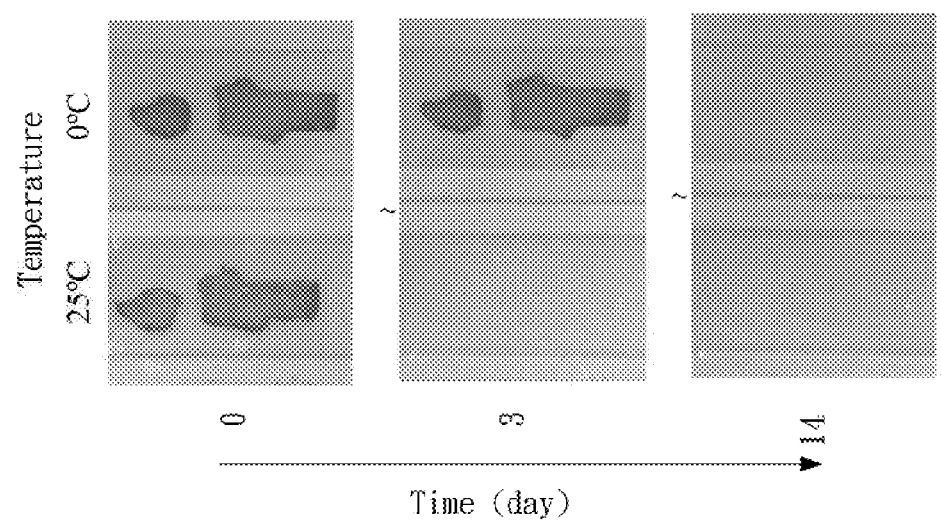
FIG. 9 shows the effect of environment temperature on color change of the time passage indicating layer tested in Example 7.

Effect of Environment Temperature on Color Change of the Time Passage Indicating Layer This example investigates the effect of temperature on the color fading of the time passage indicating layer. Time passage indicating apparatus prepared according Example 1 is placed in environment of 0° C. and +25° C., respectively, for comparison. Referring to FIG. 9, the results show that higher environment temperature would speed up the color fading process. The color fading time (of which the end point is defined as when the color of the time passage indicating layer becomes substantially the same as that of the background layer) of the sample in the +25° C. environment is 3 days; the sample in the 0° C. environment fades completely in the background after 14 days.

Example 8

Sensitivity to Light of the Time Passage Indicating Layer

Figure 10:
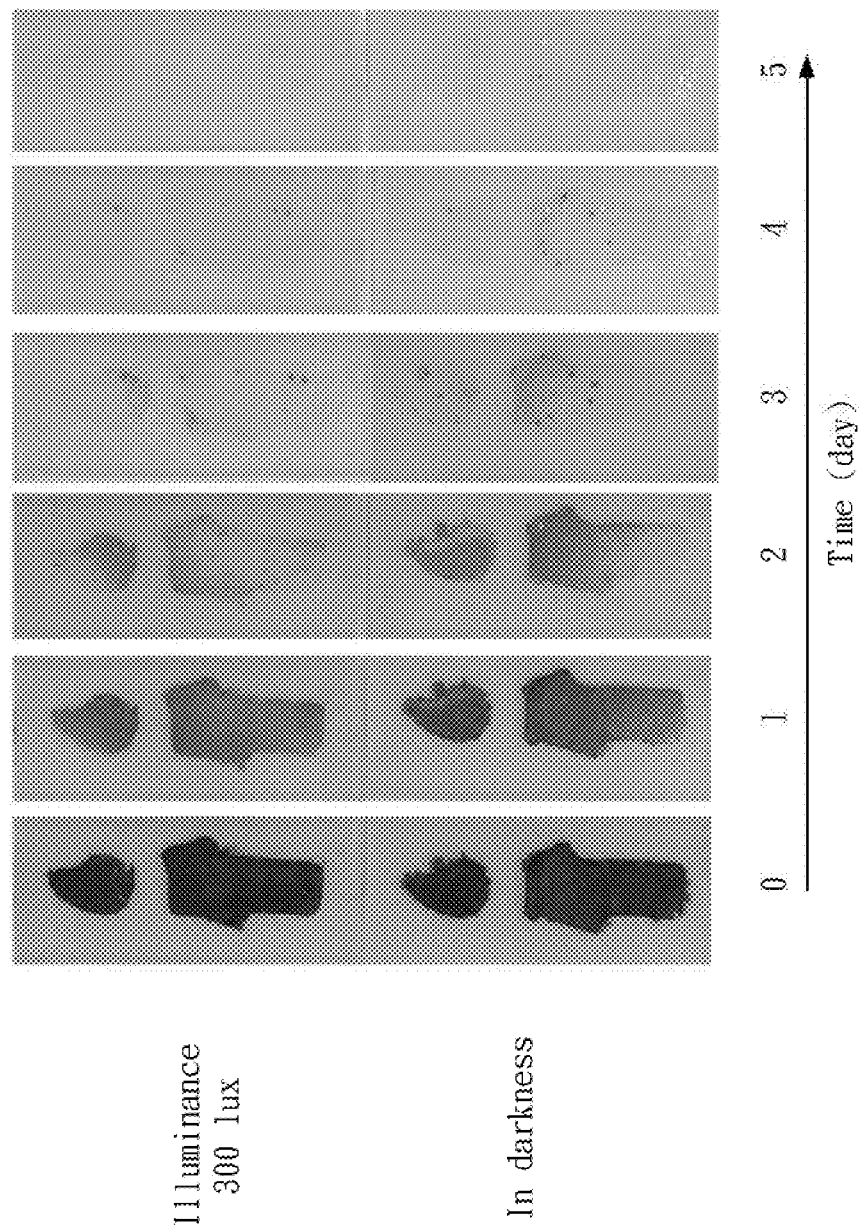
FIG. 10 shows the effect of ambient lighting on color change of the time passage indicating layer tested in Example 8.

This example investigates the sensitivity to light of the provided time passage indicating layer. The redox compound contained in the sample for test has a composition as follows: 0.025 g AQS, 0.3 g $Na_2S_2O_4$, 1.2 g NaOH (5M), and 3 g PVA (20% solution). The composition of the protection layer in the sample is as follows: 3 g Tricyclodecane dimethanol diacrylate, 3 g 2-Hydroxyethyl methacrylate, and 0.12 g Irgacure 651. The forming process of the time passage indicating apparatus is the same as that in Example 1. The formed time passage indicating apparatus is placed in darkness and a lightened environment with illuminance of 300 lux, respectively, for comparison. Referring to FIG. 10, the results show that both samples have a color fading time of 4 days. Therefore, the color change of the provided time passage indicating apparatus is not affected by light.

In summary, the present invention discloses an apparatus for indicating the passage of time. The provided apparatus functions through the change in color of a time passage indicating material whose color continuously fades throughout the oxidation process. After a time period of a predetermined length, the color of the time passage indicating material becomes substantially the same as that of a background layer, rendering an effect that the time passage indicating layer disappears from the background layer, thereby indicating the end of the time period. The present invention also discloses a method for forming the time passage indicating apparatus. Appropriate polymer binders are selected for the time passage indicating material and the background layer material to bond to each other, so the time passage indicating layer can be easily formed on the background layer by simple coating and curing procedures. Therefore, the present invention is suitable for economic industrial usage.

The foregoing description is not intended to be exhaustive or to limit the invention to the precise forms disclosed. Obvious modifications or variations are possible in light of the above teachings. In this regard, the embodiment or embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the inventions as determined by the appended claims when interpreted in accordance with the breath to which they are fairly and legally entitled.

It is understood that several modifications, changes, and substitutions are intended in the foregoing disclosure and in some instances some features of the invention will be employed without a corresponding use of other features. Accordingly, it is appropriate that the appended claims be construed broadly and in a manner consistent with the scope of the invention.

The invention claimed is:

1. An apparatus for indicating the passage of time, comprising:
    a substrate;
    a background layer formed on said substrate, said background layer being made from a first polymer binder, a base material and a background layer color rendering material, said base material being colorless and said background layer color rendering material displaying a background color such that said background layer displays said background color;
    a time passage indicating layer formed on said background layer, said time passage indicating layer covering a portion of said background layer, said time passage indicating layer being made from a solvent, a redox compound, a reducing agent and a second polymer binder wherein said second polymer binder bonds with said first polymer binder through physical or chemical bonding, said time passage indicating layer having an initial reduced state and a final oxidized state wherein said time passage indicating layer displays an initial color in said initial reduced state and a final color in said final oxidized state, said initial color is different from said final color and said final color is substantially the same as said background color, such that when in said final oxidized state, said time passage indicating layer becomes visually identifiable on said background layer to achieve an effect of said time passage indicating layer disappearing from said background layer; and
    at the beginning of the time passage to be indicated, all said redox compound in said time passage indicating layer is reduced to said initial reduced state, and later when said time passage indicating material is oxidized through contact with oxygen molecules, said time passage indicating layer gradually transforms from said initial reduced state to said final oxidized state, and the color of said time passage indicating layer changes from said initial color to said final color, when said final oxidized state is reached, said time passage indicating layer becomes visually unidentifiable on said background layer, indicating the end of the time passage to be indicated.

2. The apparatus according to claim 1, said time passage indicating layer being formed on said background layer via a time passage indicating layer forming process, said time passage indicating layer forming process comprising:

performing a time passage indicating material coating procedure to coat said solvent, redox compound, reducing agent and second polymer binder on said background layer to form a time passage indicating layer precursor, said time passage indicating layer coating procedure being performed in an oxygen-free environment; and performing a time passage indicating material drying procedure to dry said time passage indicating layer precursor to form said time passage indicating layer on said background layer, said time passage indicating material drying procedure is performed in an oxygen-free environment.

3. The apparatus according to claim 2, the method of said time passage indicating material coating procedure is selected from the group consisting of the following: spin coating, spray coating, printing, knife coating, and dip coating.

4. The apparatus according to claim 1, further comprising a protection layer, said protection layer covering said time passage indicating layer, said protection layer having at least one transparent portion such that the change in color of said time passage indicating layer is observable from the exterior of said protection layer.

5. The apparatus according to claim 4, said protection layer further comprising an oxygen-scavenging material, said oxygen-scavenging existing in said protection layer material with a predetermined composition, said oxygen-scavenging material comprising one selected from the group consisting the following, or any combination thereof: reduced metal, tannins, sulfite, ascorbate, reduced form of quinine and anthraquinone derivative, photoreducible carbonyl compound, and oxidizable organic compound.

6. The apparatus according to claim 1, further comprising a wrapper layer, said wrapper layer being oxygen-impermeable, said wrapper layer wrapping up formed said apparatus for time passage indication, said wrapper layer comprising a wrapper, said wrapper comprising a gas barrier film with a sealing layer, the material of said gas barrier film comprising one selected from the group consisting of the following, or any combination thereof: metal foil, metal oxide, carbon, $SiO_x$, polyester, polyamide, polyvinylchloride, polyvinylidene chloride, polyethylene naphthalate, polyacrylonitrile, polycarbonate, polyether, polyimide, polysulfone, rubber, and epoxy resin.

7. The apparatus according to claim 6, the material of said sealing layer comprising one selected from the group consisting of the following, or any combination thereof: polyester, polypropylene, polyvinyl alcohol, polyvinyl acetate, rubber, epoxy resin, and polyethylene.

8. The apparatus according to claim 1, said reducing agent being sodium hydrosulfite or a mixture of sodium hydrosulfite and alkaline medium.

9. The apparatus according to claim 1, the material of said substrate comprising one selected from the group consisting of the following, or any combination thereof: aluminum metallized plastic, aluminum metallized paper, metal oxide coated plastic, metal oxide coated paper, glass, metal, plastic, and paper.

10. The apparatus according to claim 1, said solvent comprising one selected from the group consisting of the following, or any combination thereof: water and alcohol.

* * * * *